(12) United States Patent
Vinogradov et al.

(10) Patent No.: US 10,352,909 B2
(45) Date of Patent: Jul. 16, 2019

(54) PAIRED MAGNETOSTRICTIVE TRANSDUCERS FOR NON DESTRUCTIVE TESTING OF TUBULAR STRUCTURES WITH SELECTIVE TORSIONAL OR FLEXURAL WAVE MODES

(71) Applicant: Southwest Research Institute, San Antonio, TX (US)

(72) Inventors: Sergey A Vinogradov, San Antonio, TX (US); Charles Duffer, San Antonio, TX (US); Glenn M. Light, San Antonio, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 228 days.

(21) Appl. No.: 15/650,685

(22) Filed: Jul. 14, 2017

(65) Prior Publication Data
US 2019/0017971 A1 Jan. 17, 2019

(51) Int. Cl.
*G01N 29/24* (2006.01)

(52) U.S. Cl.
CPC . *G01N 29/2412* (2013.01); *G01N 2291/0258* (2013.01); *G01N 2291/044* (2013.01); *G01N 2291/0426* (2013.01); *G01N 2291/0427* (2013.01); *G01N 2291/267* (2013.01); *G01N 2291/2636* (2013.01)

(58) Field of Classification Search
CPC ....... G01N 29/2412; G01N 2291/0427; G01N 2291/044; G01N 2291/267; G01N 2291/0258; G01N 2291/0426; G01N 2291/2636
USPC .......................................................... 73/627
See application file for complete search history.

(56) References Cited

U.S. PATENT DOCUMENTS

| | | | | |
|---|---|---|---|---|
| 5,808,202 | A * | 9/1998 | Passarelli, Jr. | ..... G01N 29/2412 702/36 |
| 6,109,108 | A * | 8/2000 | Ohtani | ...................... B06B 1/04 73/599 |
| 7,821,258 | B2 | 10/2010 | Vinogradov | |
| 8,098,065 | B2 * | 1/2012 | Kwun | ................ G01N 29/2412 324/240 |
| 9,170,239 | B2 * | 10/2015 | Vinogradov | ....... G01N 29/2412 |
| 2003/0205088 | A1 * | 11/2003 | Passarelli, Jr. | ....... G01N 29/223 73/643 |
| 2004/0035221 | A1 * | 2/2004 | May | ........................ G01D 5/14 73/862.331 |
| 2017/0115204 | A1 | 4/2017 | Vinogradov | |

* cited by examiner

*Primary Examiner* — Jacques M Saint Surin
(74) *Attorney, Agent, or Firm* — Livingston Law Firm (57) ABSTRACT

Various embodiments of magnetostrictive transducers (MsTs) for detecting defects in a tubular structure comprise one or more AC coils and one or more magnets. The transducer has a pair of coils (or two coil elements), which are spaced 180 degrees apart relative to the circumference of the tubular structure. Each MsT is selectively operable or configurable so that it may generate either torsional or flexural guided waves.

9 Claims, 14 Drawing Sheets

PAIRED MAGNETOSTRICTIVE TRANSDUCERS FOR NON DESTRUCTIVE TESTING OF TUBULAR STRUCTURES WITH SELECTIVE TORSIONAL OR FLEXURAL WAVE MODES

TECHNICAL FIELD OF THE INVENTION

This invention relates to nondestructive testing using guided wave testing (GWT), and more particularly, method of using magnetostrictive electromagnetic acoustic transducers for such testing.

BACKGROUND OF THE INVENTION

Many processing plants, such as refineries, chemical plants, and electric power generation plants, use networks of pipelines. Failure of these pipelines can cause major disruption of plant operation and an unscheduled outage. To ensure safe operation of such plants, there is a need for on-line non destructive testing methods to inspect and monitor pipelines.

One effective method for inspecting and monitoring a long length of pipelines is guided wave testing (GWT) using a magnetostrictive transducer (MsT). A common implementation of this method uses primarily torsional waves (T-waves) that are generated in a thin ferromagnetic strip placed around or in the pipe under test. MsT testing can also be achieved with direct generation of waves in the tested structure via electromagnetic force.

The generated waves propagate along the pipe and are partially reflected by geometric irregularities present in the pipeline, such as welds or corrosion defects. The reflected signals are then detected in a pulse-echo mode. From the arrival time of the reflected signal and the signal amplitude, the axial location of the irregularity and its severity are determined. In above-ground pipelines, this method can detect 2% to 3% defects over 500 feet from a sensor location. The % refers to the defect's cross-sectional area relative to the total cross section of the pipe wall.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION OF THE INVENTION

As described in the Background, common implementations of magnetostrictive transducer (MsT) testing for pipelines use primarily torsional waves (T-waves) that are generated in a thin ferromagnetic strip placed on or near the structure being tested, or directly generated in the tested structure using electromagnetic excitation. To produce T-waves, the MsT testing requires a perpendicular relationship between DC bias magnetic fields needed for MsT operation and AC magnetic fields applied to generate waves.

In the examples of this description, the MsT method is discussed in terms of non-destructive testing (inspection and/or monitoring) of cylindrical structures such as pipelines, that are made of ferromagnetic material. The methods are not limited to pipelines, and can be used to test any shape of "tubular structure" (abbreviated herein as "tube"), with a cross sectional geometry that can be circular, rectangular or other, and can be closed or open-channeled.

Thus, the following description is directed to nondestructive testing of ferromagnetic tubular structures using magnetostrictive transducers (MsTs) and electromagnetic transduction. Most of the embodiments described herein are for use with tubular structures for which access to the inside of the tube can be obtained. The inner diameter of the tubular structure may be as small as a few millimeters to as large as a few meters.

In general, the testing process begins with inserting an MsT probe into the tube. The probe carries the MsT along the length of the tube, and the MsT transmits guided waves along the tube walls. The guided wave reflections are received, and data is collected. Then, the probe is removed.

Existing MsTs for testing tubular structures by being placed inside the structure are described in U.S. Pat. No.

7,821,258, entitled "Method and System for Generating and Receiving Torsional Guided Waves in a Structure", to Vinogradov, incorporated by reference herein.

Conventional In-Tube MsT Testing

Figure 1:
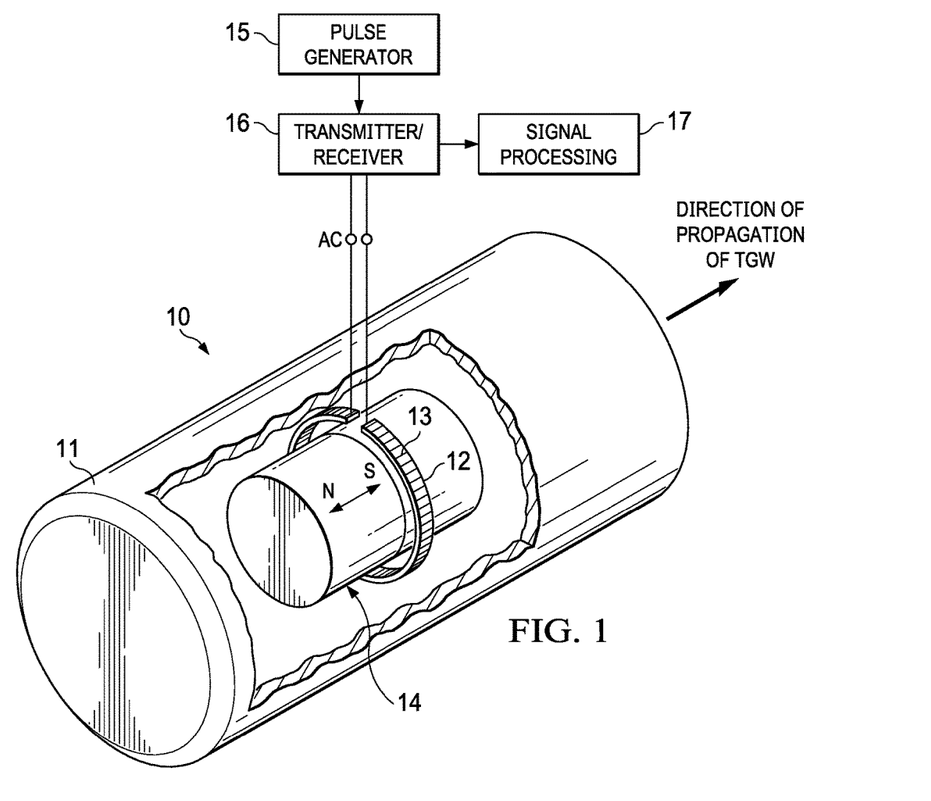
FIG. 1 illustrates the principle of electromagnetic wave generation, using a magnetostrictive transducer (MsT) placed inside a tubular structure.

FIG. 1 illustrates the principle of MsT guided wave testing, using an MsT 10 placed inside a tube 11. The conventional MsT 10 of FIG. 1 comprises a ring-shaped ferromagnetic strip 12, with an AC coil 13 wrapped around its short dimension (width). A permanent magnet 14 is located inside the coil 13 with its poles parallel to the long dimension of the tube. The permanent magnet 14 creates a bias magnetic field in the direction indicated.

Ferromagnetic strip 12 acts as a shielding material, diminishing the time varying magnetic field produced by the portion of the AC coil 13 located on the inner surface of the strip 12. The portion of the AC coil 13 facing the inner diameter of the tube will produce a time varying magnetic field.

When activated, AC coil 13 generates an alternating field that is perpendicular to the bias magnetic field. The direction of the permanent magnetic bias field, as well as the orientation of the windings of the AC coil 13, are parallel to the direction of propagation of transversal vibration.

In a completed system, with a pulse generator 15 creating an AC pulse that is delivered through transmitter/receiver 16 to AC coil 13, an impulse of alternating current is created in AC coil 13. This impulse of alternating current creates an alternating magnetic bias in tube 11, which in turn causes torsional guided waves (TGW) to propagate in the direction indicated.

If there is a defect in tube 11, a reflected torsional guided wave will be reflected back towards the AC coil 13 causing oscillations of magnetic domains in the wall of tube 11. The AC coil 13 will respond with what is known as the inverse Wiedemann effect, which will cause a mechanical impulse in AC coil 13. The reflected torsional guided wave signal detected in AC coil 13 is received by transmitter/receiver 16 and delivered to signal processor 17, which analyzes the signal to locate and estimate the size of the defect.

Dual Coil MsTs with Torsional and Flexural Wave Modes

As explained below in connection with FIG. 2 and following, instead of a single AC coil evenly distributed around the tube's inner circumference as in FIG. 1, the MsTs described herein have a pair of AC coils (or two coil elements) covering only segments of the tube's inner circumference. The coils are activated at the same time, and depending on the magnetization pattern and whether the coils are connected in phase or out of phase, the MsT generates either fundamental torsional or flexural wave modes.

Unlike torsional guided waves, flexural waves have a non-uniform profile of energy distribution around the circumference of the tube. For this reason, they have a selective sensitivity to any anomalies located in certain quadrants around the tube's circumference and can be used for characterizing the circumferential extent of the anomaly.

Figure 1A:
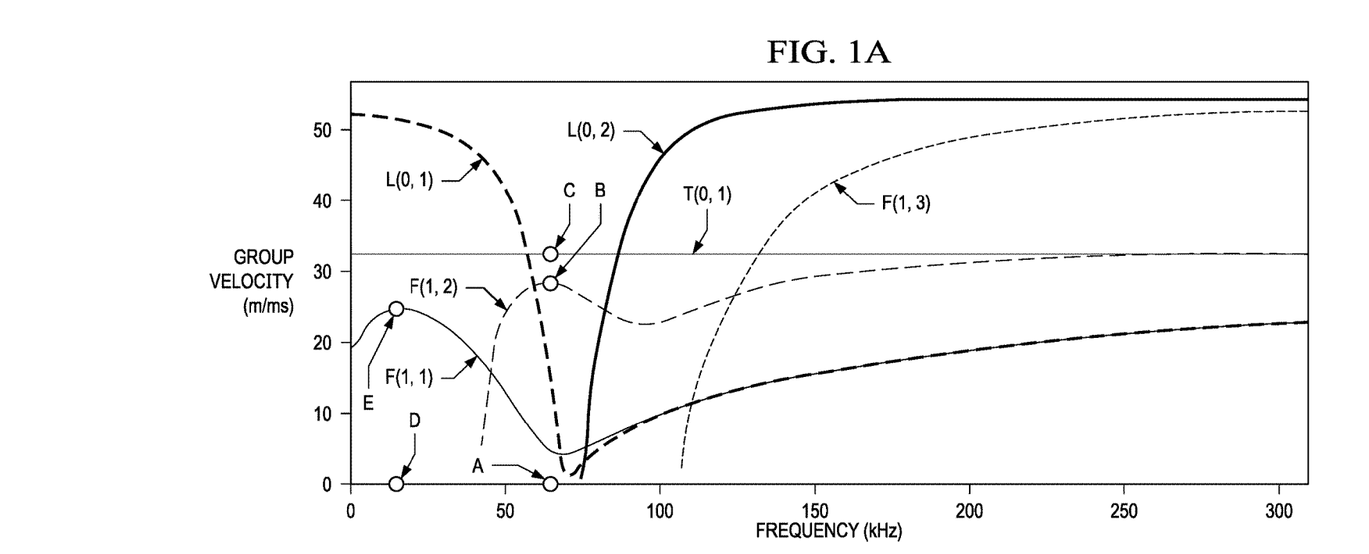
FIG. 1A illustrates dispersion curves for torsional and flexural waves in an example tube wall.

As an example, FIG. 1A illustrates dispersion curves for a one-inch outer diameter tube with a 1.5 mm wall thickness. The fundamental torsional wave is marked as T(0,1) and has a constant velocity of about 3200 m/s in all frequency ranges. The group velocity of flexural guided waves depends on frequency. There are different types of flexural guided waves, such as F(1,1) with the peak velocity 2400 m/s at 16 kHz (point E), or F(1,2) mode with the local peak velocity 2800 m/s at about 60 kHz.

Figure 1B:
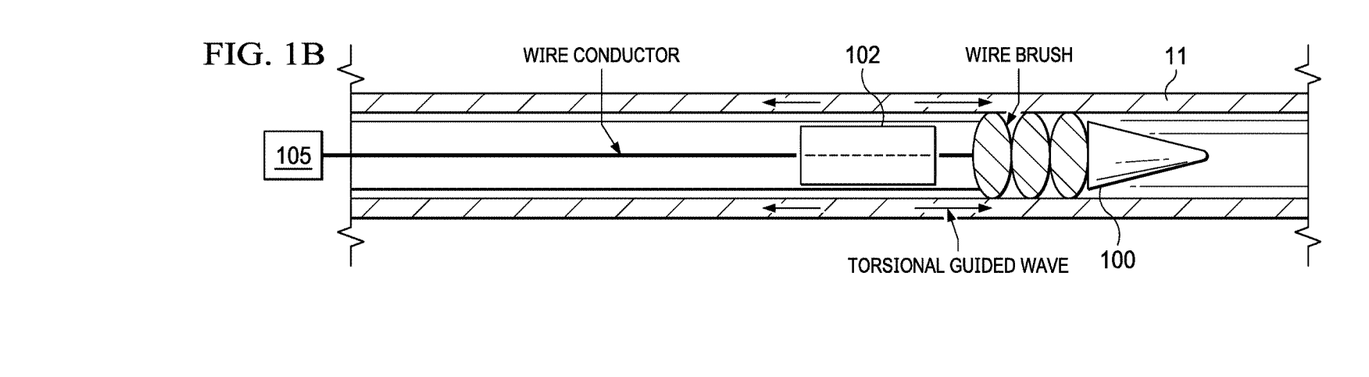
FIG. 1B illustrates a probe suitable for carrying an magnetostrictive transducer (MsT) down the inner length of a tube.

FIG. 1B illustrates a probe 100 inserted into a tube 11. Probe 100 carries an MsT 102 along the length of the tube, and can be positioned at a series of distances from the end of the tube to allow measurement waves to be generated and reflections received. Various configurations of MsT 102 are described below, with one or more coils and one or more permanent magnets. The diameter of probe 100 and the size of the MsT 102 are appropriate for the diameter of the tube 11. That is, it is typically desired that the MsT elements be near the wall of tube 11.

Control unit 15 contains the pulse generator 105 and other electronics described above in connection with FIG. 1. Control unit 105 is electrically connected to MsT 102, and as explained below, is operable to reverse the current flow in at least one of the coils. The MsT 102 generates guided waves, which are selectively either torsional or flexural. A torsional guided wave is illustrated.

Dual Coils with Center Biasing Magnet

Figure 2:
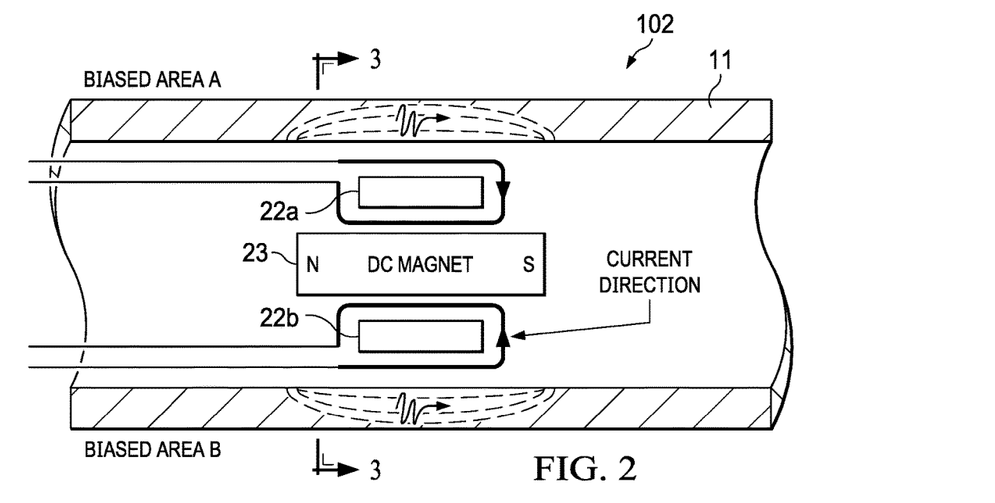
FIG. 2 is a cross sectional view, along the center axis of a tube, illustrating an MsT having dual coils and a center magnet and operating with the coil currents in the same direction.
Figure 3:
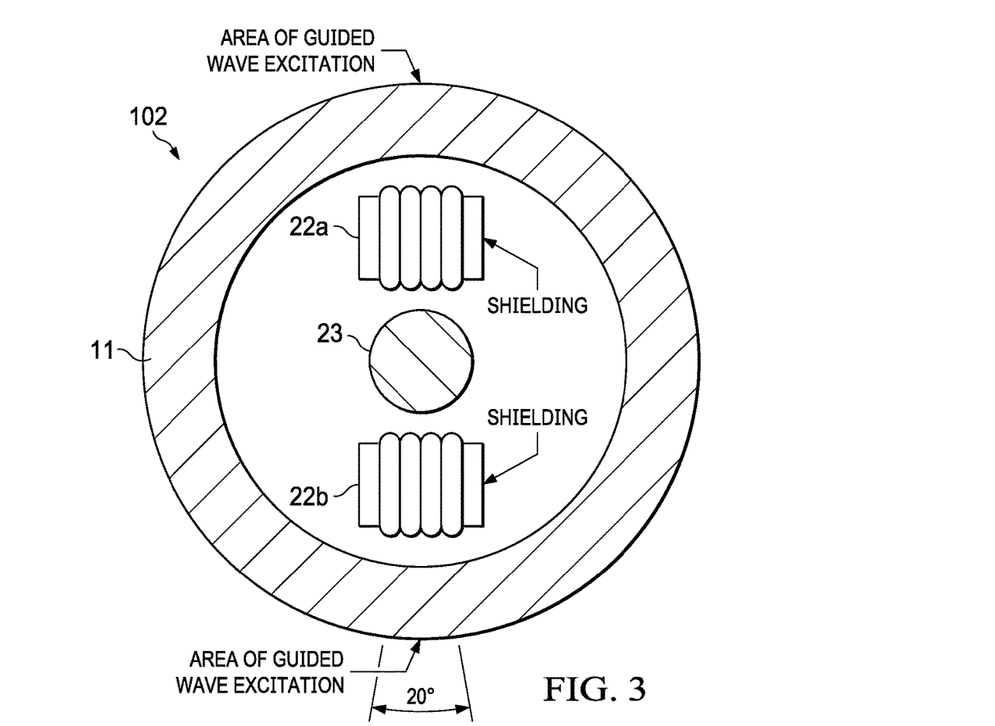
FIG. 3 illustrates the MsT of FIG. 2, along line A-A.

FIGS. 2 and 3 illustrate a dual coil MsT 20 inserted into a tube 11 using a probe such as probe 100. FIG. 2 is a side view, cross sectioned along the center axis of tube 11, and FIG. 3 is a cross sectional view along A-A. Although not explicitly illustrated, it is assumed that MsT 20 and the other MsT's described herein have whatever housing and attachment means as are suitable for use inside probe 100.

As depicted, in these various embodiments, the elements of the MsT, i.e., its coil(s) and magnet(s), are positioned within the probe such that they are near, but not touching the walls of the tube 11. The coils are further positioned such that they are centered 180 degrees apart from each other, relative to the inner circumference of the tube.

Coils 22a and 22b may be wrapped around any ferromagnetic or non-ferromagnetic material. For each coil, this results in shielding, such that the magnetic fields produced by the portion of the coil behind the shield does not interact with the tubular structure 11. To shield high frequencies, a non-ferromagnetic material, such as aluminum, may be desired. With shielding, coil 22a (side of the coil facing the tube) generates a useable magnetic field with magnetic field produced by the side of the coil facing the tube cancelled out. At the same time coil 22b (side of the coil facing the tube) generates a useable magnetic field with magnetic field produced by the side of the coil facing the tube cancelled out.

AC coils 22a and 22b are located 180 degrees apart, relative to the inner circumference of tube 21. Coils 22a and 22b are quite narrow in width, and each corresponds to only a radial fraction of the inner circumference of the tube. As shown in FIG. 3, an example of a suitable radial fraction is 20 of the 360 degree inner circumference. It is expected that in practice, each coil will have a width corresponding to 30 degrees or less of the inner circumference of the tubular structure. Because each coil is narrow and can have multiple turns of wire, the current density produced by each coil can be high and optimized for operation in tubes made from ferromagnetic alloys such as Seacure, Duplex, carbon steel, or other ferromagnetic alloys.

Figure 4:
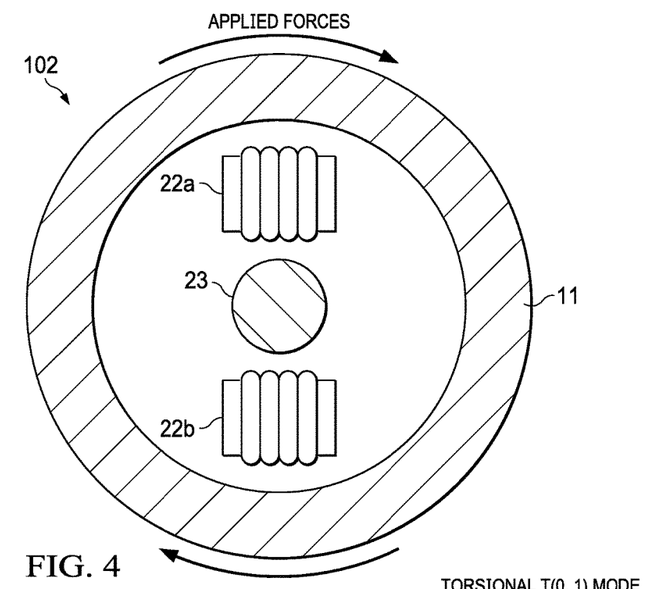
FIG. 4 illustrates the applied forces of the MsT of FIG. 2.
Figure 5:
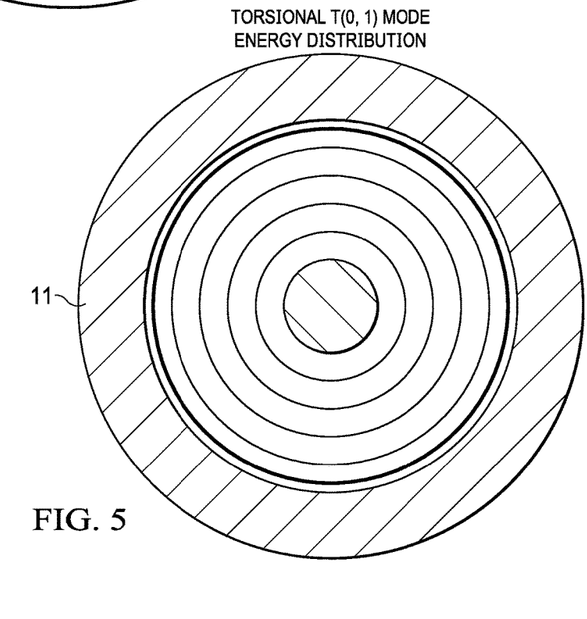
FIG. 5 illustrates the torsional mode energy distribution of the MsT of FIG. 2.

FIGS. 4 and 5 illustrate the applied forces and energy distribution, respectively, resulting from coils 22a and 22b when activated. When the currents in coils 22a and 22b flow in the same direction relative to the tube walls and to each other, because of unidirectional bias magnetization of the tube in the areas adjacent to the coils (biased area A and biased area B shown in FIG. 2), MsT 102 will produce forces applied to the same direction around the tube circumference, as shown in FIG. 4. Such a force distribution will produce an axially symmetric torsional guided wave, as shown in FIG. 5.

Figure 6:
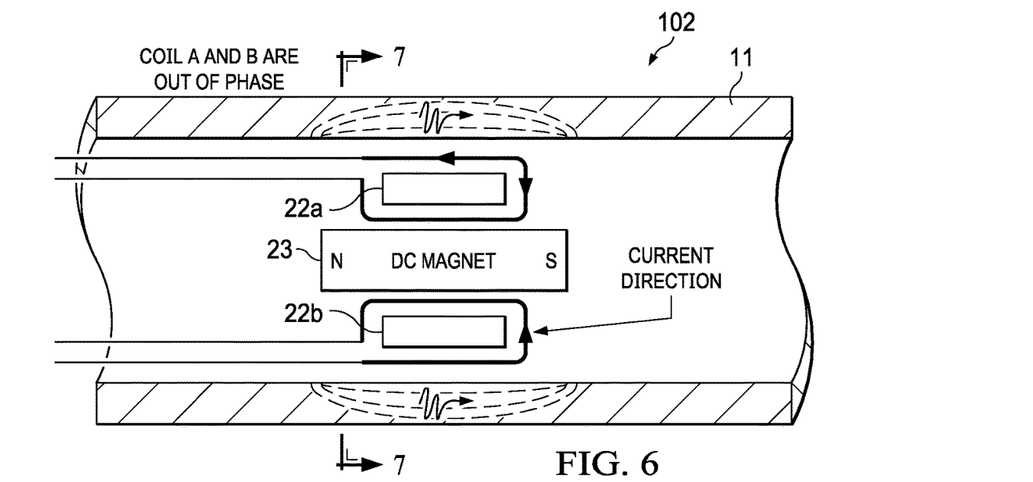
FIG. 6 is a cross sectional view, along the center axis of a tube, illustrating an MsT like that of FIG. 2, but operating with the coil currents in opposite directions.

FIG. 6 illustrates an alternative mode of operation of MsT 102. Using control unit 105, AC coils 22a and 22b are activated such that their currents flow in opposite directions. This out of phase operation results in flexural guided wave modes.

Figure 7:
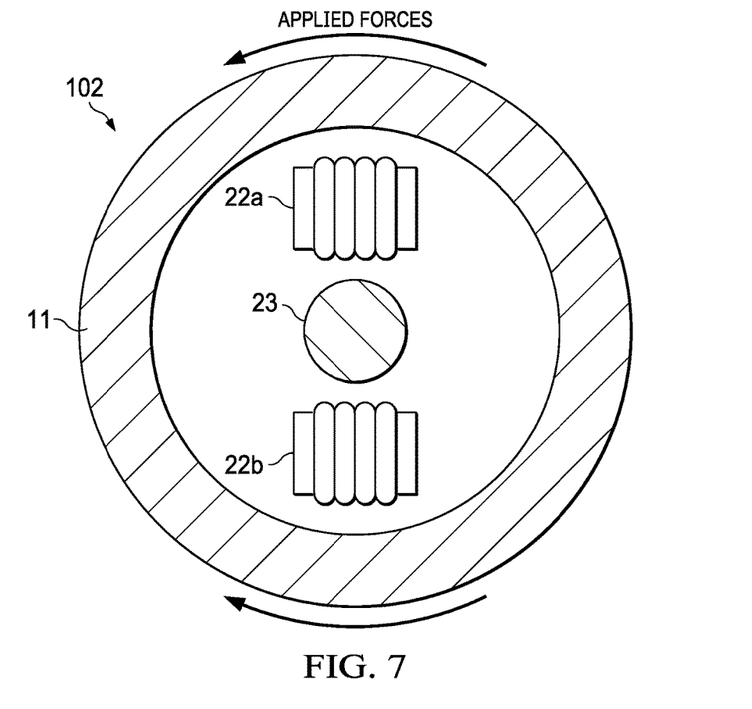
FIG. 7 illustrates the applied forces of the MsT of FIG. 6.
Figure 8:
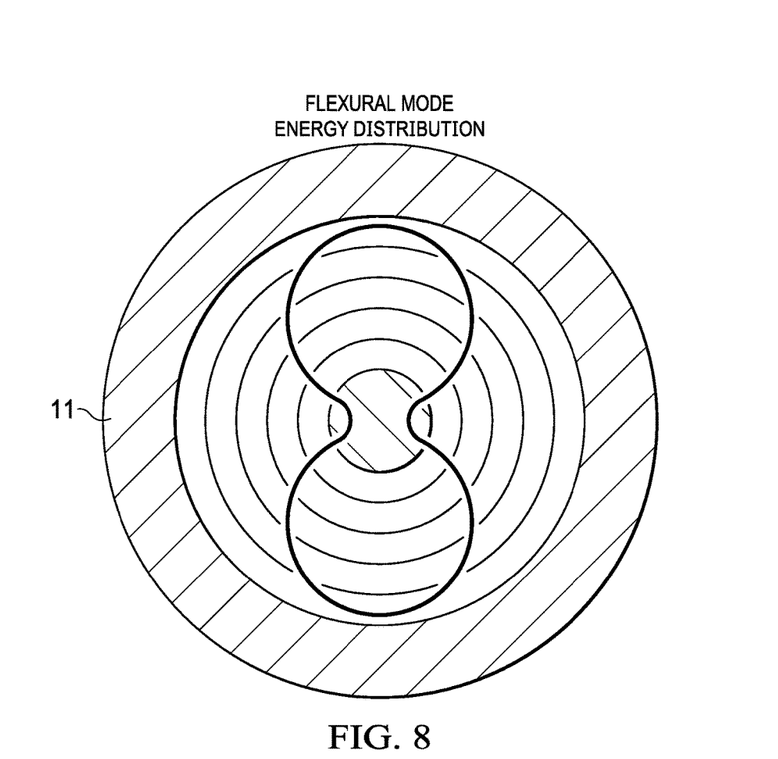
FIG. 8 illustrates the flexural mode energy distribution of the MsT of FIG. 7.

FIGS. 7 and 8 illustrate the applied forces and energy distribution, respectively, resulting from coils 22a and 22b if the current directions of the coils 22a and 22b are in opposite directions. The patterns of applied forces and energy distribution are non-axially symmetric.

Dual Coils with Side Biasing Magnets

FIGS. 9-14 illustrate an MsT 90 having dual coils 22a and 22b, which may be used within an MsT probe 100 and selectively activated for torsional or flexural wave modes as in the embodiments of FIGS. 2-8. However, MsT 90 has side biasing magnets 93a and 93b instead of a center magnet. Magnets 93a and 93b have polarizations perpendicular to the axis of tube 11, and in opposite directions relative to each other. Because magnets 93a and 93b are located on the sides of coils 92a and 92b, they can be larger and provide a stronger biasing field compared to a center magnet. Also, the side magnets 93a and 93b leave more space for AC coil windings.

As with the center magnet embodiment of FIGS. 2-8, MsT 90 can provide generation of either torsional or flexural guided waves by selectively operating control unit 105.

Figure 9:
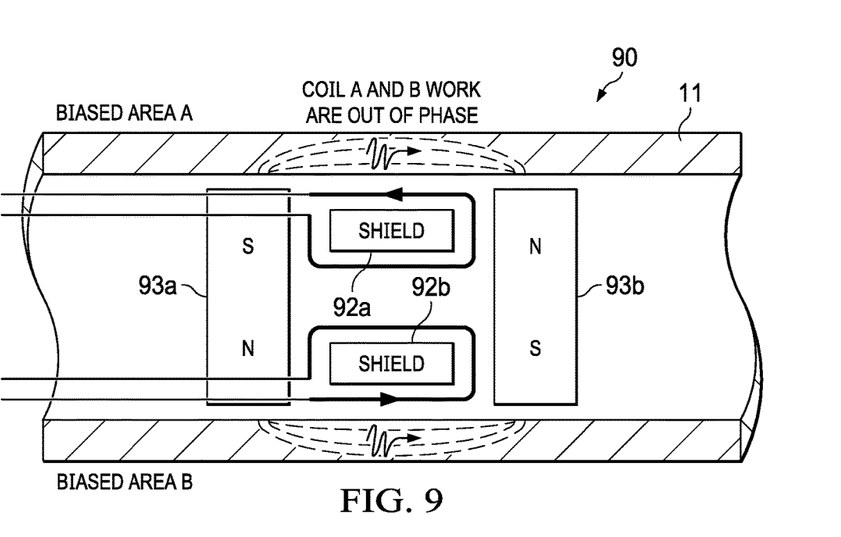
FIG. 9 is a cross sectional view, along the center axis of a tube, illustrating an MsT having dual coils and side magnets and operating with the coil currents in opposite directions.
Figure 10:
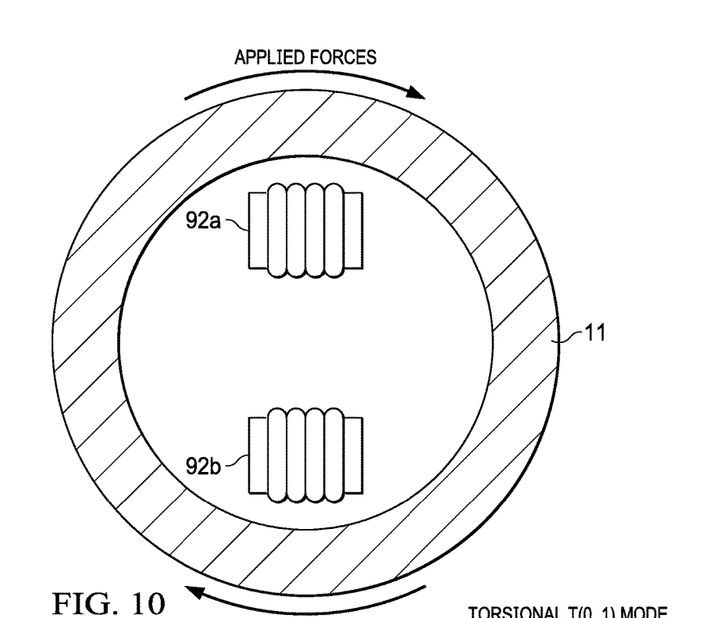
FIG. 10 illustrates the applied forces of the MsT of FIG. 9.
Figure 11:
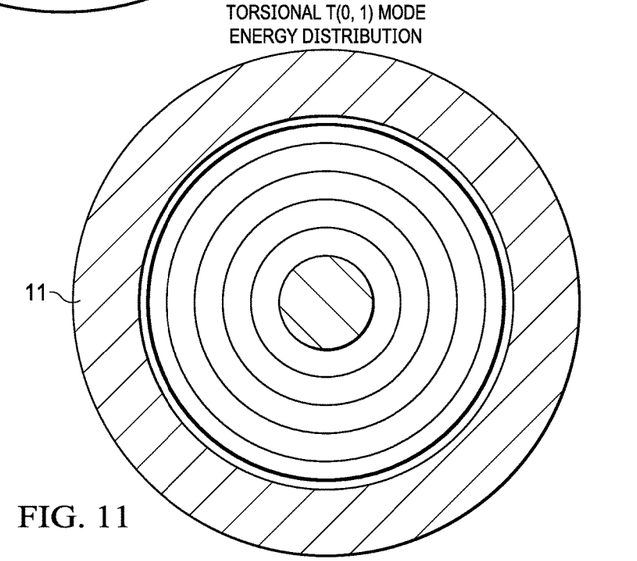
FIG. 11 illustrates the torsional mode energy distribution of the MsT of FIG. 9.

In FIG. 9, coils 92a and 92b are activated to operate out-of-phase, and MsT 90 generates a torsional guided wave. FIGS. 10 and 11 illustrate the applied forces and energy distribution of MsT 90 activated in this manner.

Figure 12:
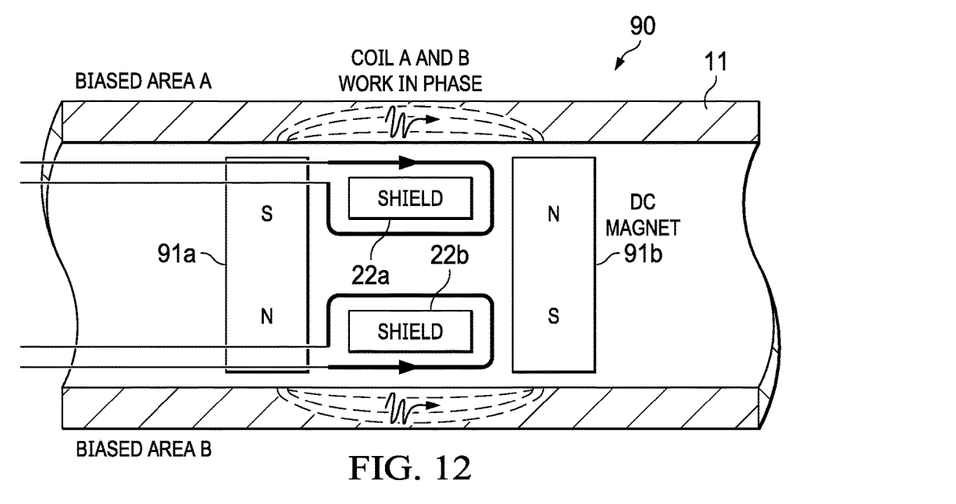
FIG. 12 is a cross sectional view, along the center axis of a tube, illustrating an MsT like that of FIG. 9, but operating with the coil currents in the same direction.
Figure 13:
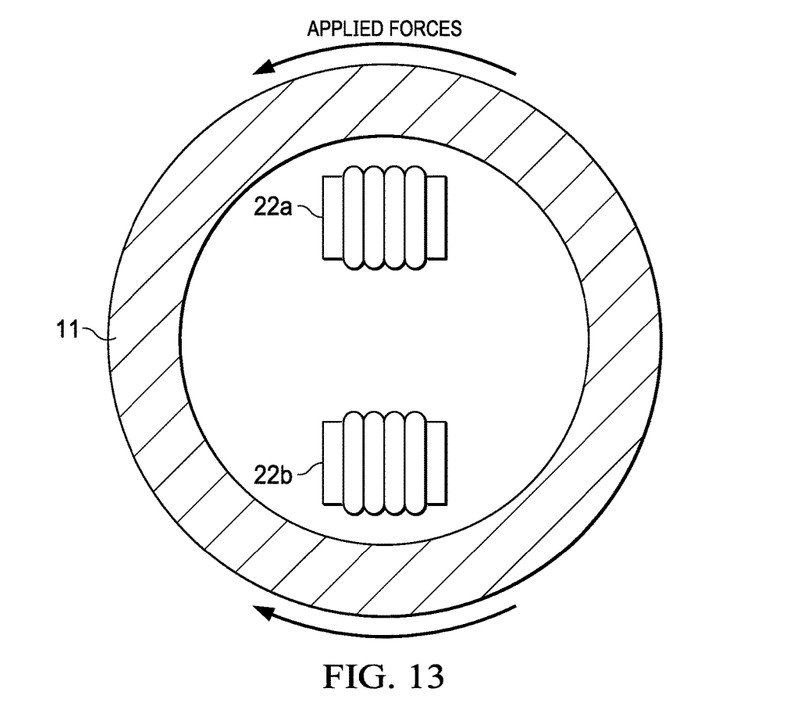
FIG. 13 illustrates the applied forces of the MsT of FIG. 12.
Figure 14:
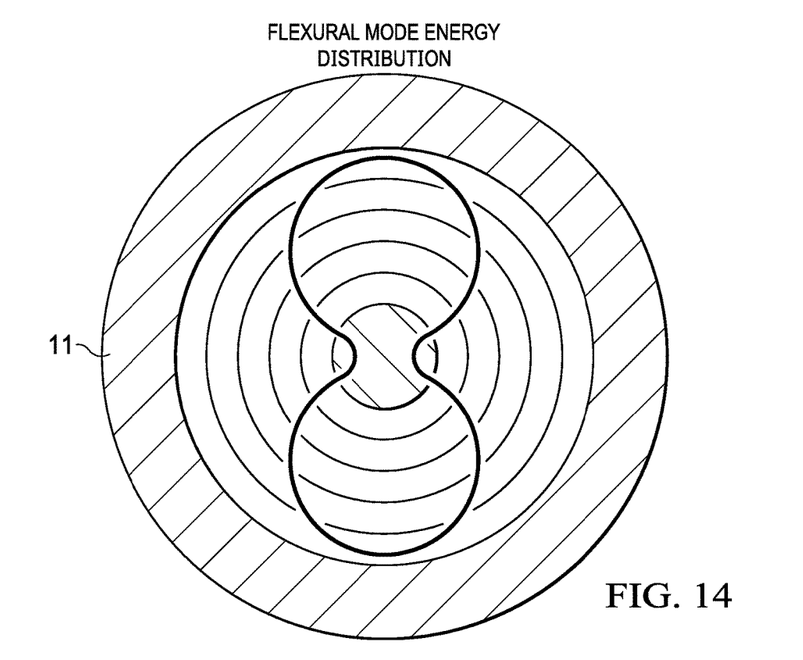
FIG. 14 illustrates the flexural mode energy distribution of the MsT of FIG. 9.

In FIG. 12, coils 92a and 92b are activated to operate in-phase, and MsT 90 generates flexural guided waves. FIGS. 13 and 14 illustrate the applied forces and energy distribution of MsT 90 activated in this manner.

Single Coil without Shielding, with Center or Side Magnets

Figure 15:
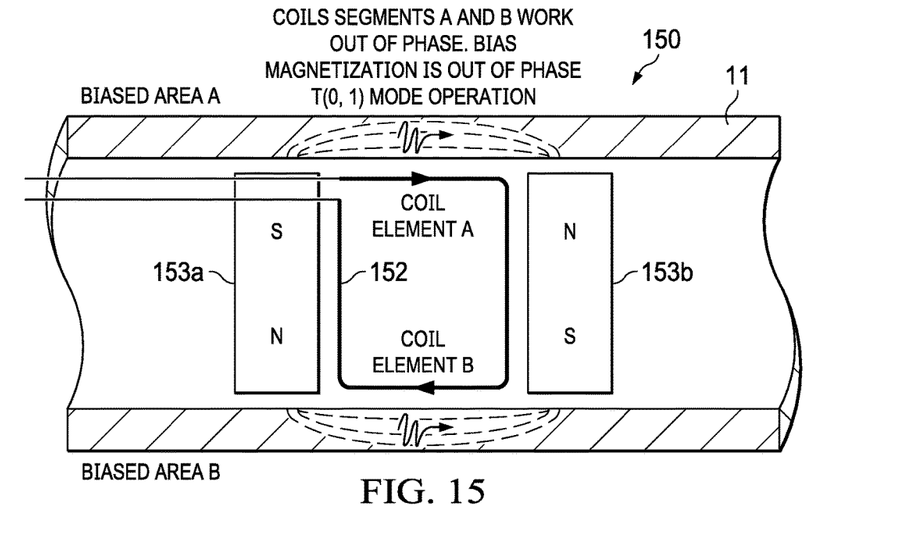
FIG. 15 is a cross sectional view, along the center axis of a tube, illustrating an MsT having a single coil and side magnets.
Figure 16:
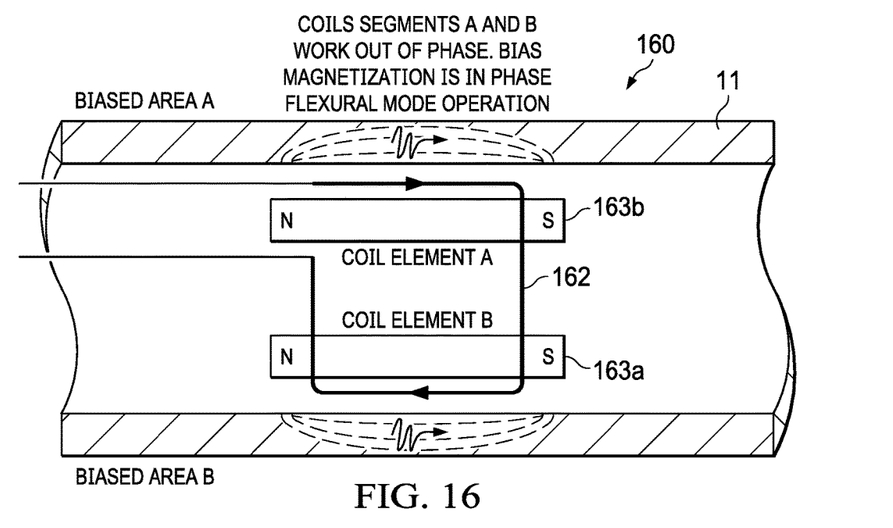
FIG. 16 is a cross sectional view, along the center axis of a tube, illustrating an MsT having a single coil and two inside magnets.

FIGS. 15 and 16 illustrate additional embodiments of an MsT for use with probe 100 and inserted into a tube 11. MsT 150 and MsT 160 each comprise a single coil 152 and 162, respectively, with the coil not wrapped around shielding material. The coil 152 or 162 may be wrapped around a nonconductive material, such as a plastic or Delrin. In the embodiments of FIGS. 15 and 16, each of two portions of coil 152 or 162 (elements A and B) acts as an active coil on opposite sides of the tubular structure 11. The absence of shielding material reduces the coil length, and as a consequence, its impedance. As a result, the coil has increased effectiveness.

In FIG. 15, MsT 150 has magnets 153a and 153b placed on either side of coil 151. Magnets 153a and 153b are polarized in directions perpendicular to the length of the tube 11, but opposite from each other (out of phase). Coil elements A and B operate out-of-phase and the biasing fields in areas A and B are also out-of-phase, and MsT 150 generates torsional guided waves. If one of the magnets is rotated, such that the polarizations of permanent magnets 153a and 153b are the same, MsT 150 will produce flexural waves.

In FIG. 16, MsT 160 has magnets 163a and 163b placed inside coil 150 and polarized in the same direction along the length of the tube (in-phase). MsT 160 produces flexural guided waves. MsT 160 can produce torsional waves if one of the magnets 163a or 163b is rotated so that the magnets are oppositely polarized.

Dual Coils Rotated Radially

Figure 17:
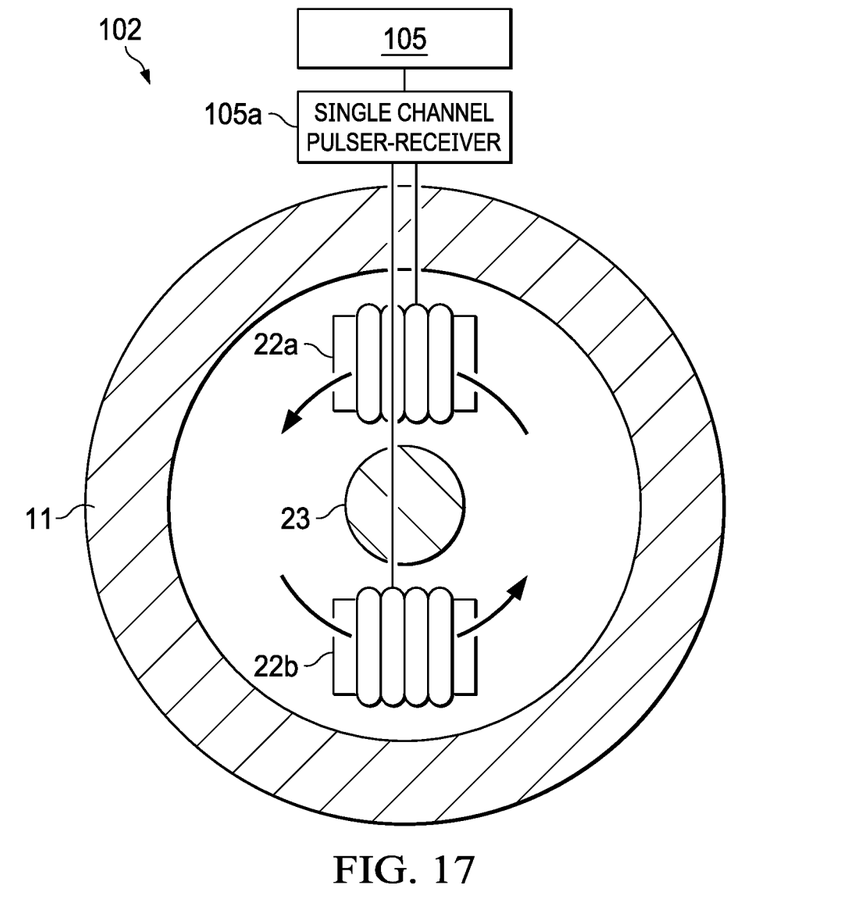
FIG. 17 is a cross sectional view of a tube, illustrating an MsT like that MsT of FIG. 2, but being turned around in the radial direction within the tube.

FIG. 17 illustrates the MsT 20 of FIG. 2, in cross section as in FIG. 3, but with probe 100 being turned inside the tubular structure 11 in a radial direction. This results in moving the coils 22a and 22b around the inner circumference of the tubular structure 11.

Figure 18:
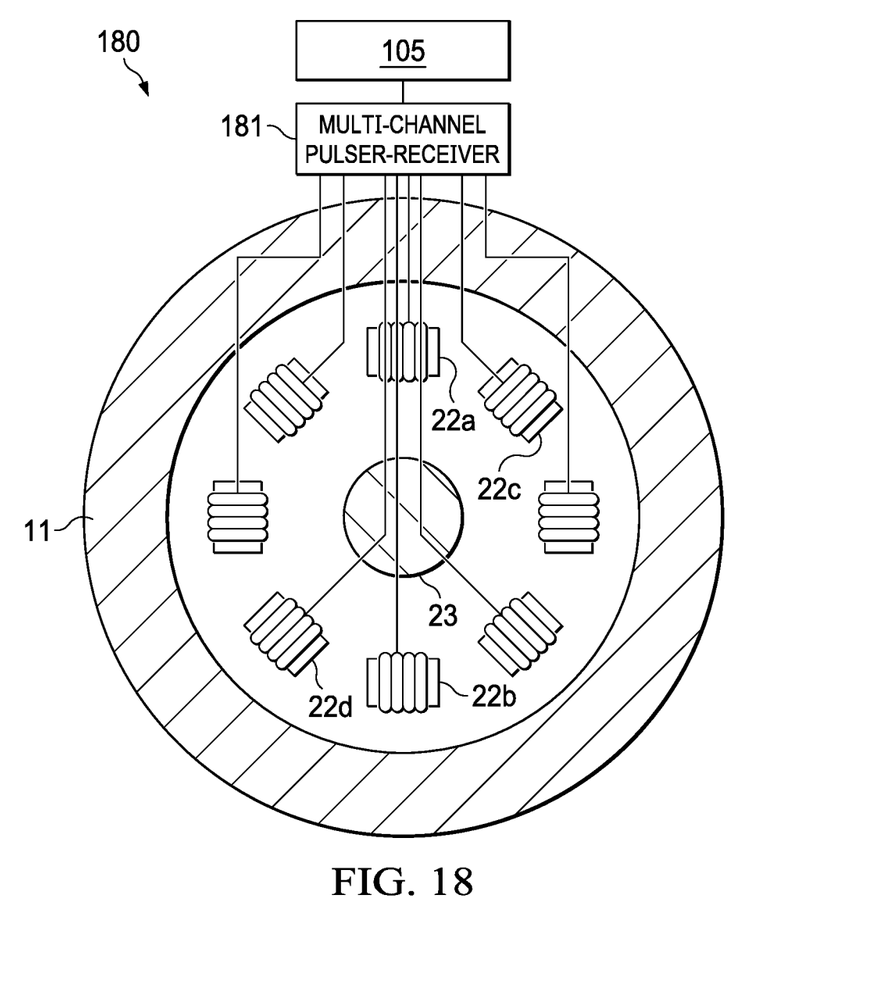
FIG. 18 is a cross sectional view of a tube, illustrating four pairs of MsTs like that MsT of FIG. 2.

FIG. 18 illustrates a similar concept as FIG. 17, but with multiple coil pairs, 22a/22b, 22c/22d etc., around the inner circumference of tube 21. These coils are activated in pairs.

Referring to FIG. 17, an advantage of using a single pair of coils 22a and 22b is that only a single channel pulser/receiver 105a can be used to acquire data. Referring to FIG. 18, with multiple coil pairs, a multi-channel pulser/receiver 181 is needed (or single channel equiment with a multiplexer). With the configuration of FIG. 18, a first A-scan should be acquired using coils A and B, the second A-scan should be acquired using the pair of coils C and D, and so on.

Because each coil 22a etc. activates only a narrow segment of the tube on the opposite sides of the tube/pipe walls at a time, each A-scan can be attributed to the corresponding area of the tube. As a result of this, the image provided by MsT 20 will be polarized vertically, horizontally, or by a choosen angle.

Combining the scans together, the data can be used to form a "B-scan" image of the tube's condition, helping to identify the circumferential position and the circumferential extent of anomalie. Because T-mode is in an axially symmetrical mode, it quickly spreads around the tube circumference and even a localized anomaly will produce a response covering the entire circumference of the tube. Even non-axially symetric anomalies will produce an axially symetric response. Unlike the T-mode, the flexural mode produces a peak of energy distribution that corresponds with the circumferential position of the anomaly. This provides information about the location of the anomaly around the tube circumference.

Dual Coils for Use on Outer Surface of Tube

Figure 19:
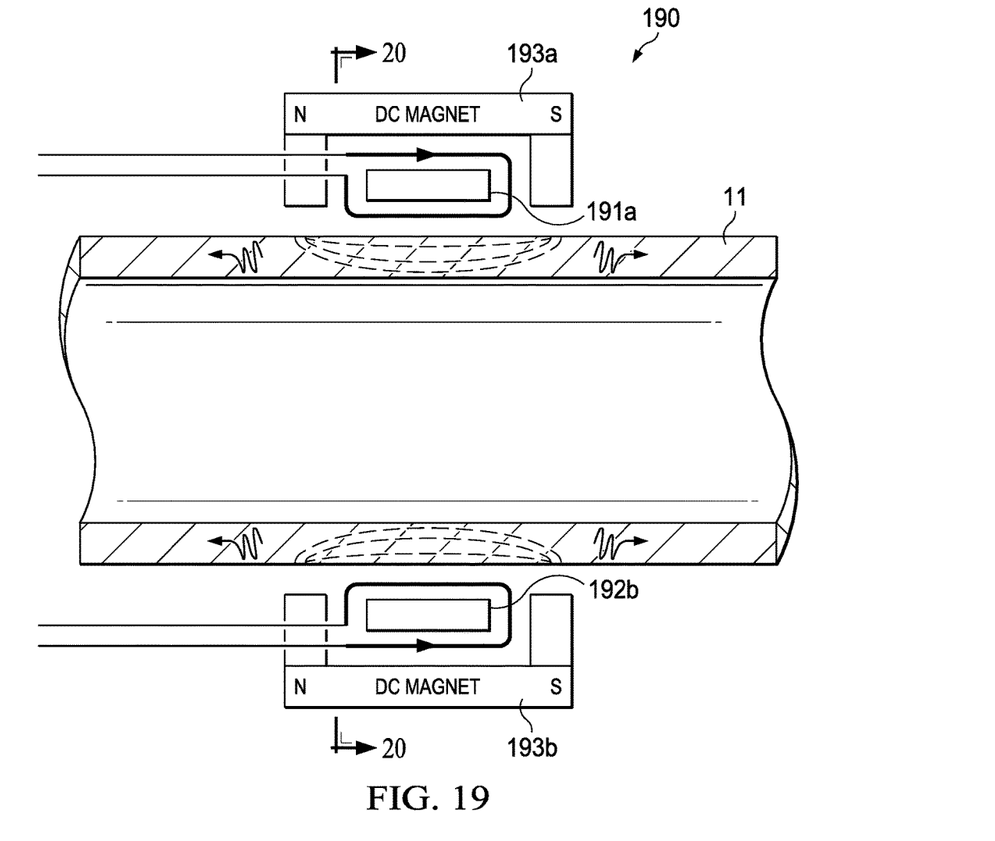
FIG. 19 is a cross sectional view, along the center axis of a tube, illustrating an MsT for use on the outside of a tube.
Figure 20:
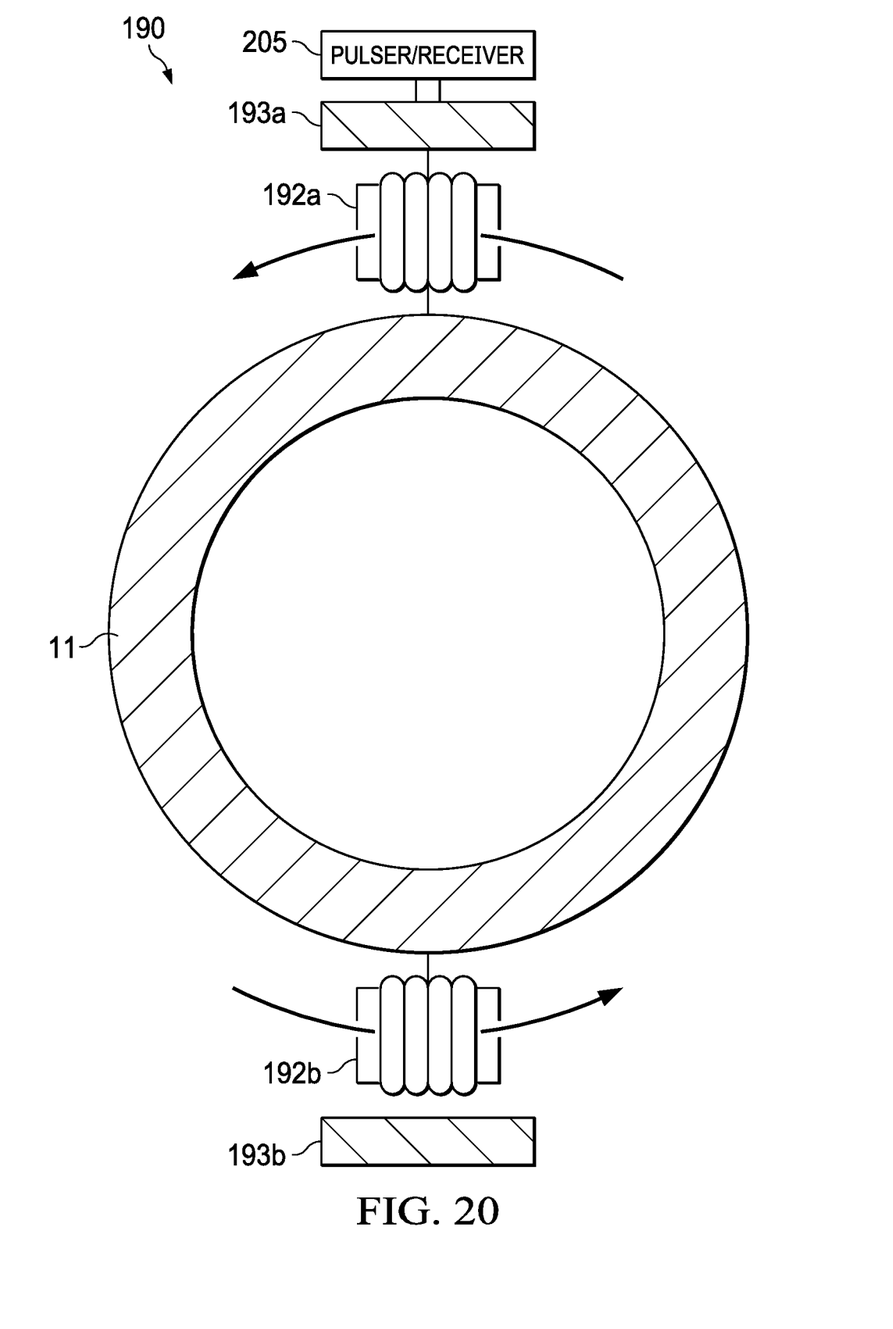
FIG. 20 illustrates the MsT of FIG. 19, along line A-A.

FIGS. 19 and 20 are a mid-axis cross-sectional view and a circumferential cross-sectional view, respectively, of an MsT 190 for use when only access from the outside surface of the tube is available. In this case, the coils 192a and 192b and the permanent magnets 193a and 193b can be located outside of the tube 11, adjacent to its outer surface. The coils 192a and 192b are positioned such that they arre centered 180 degrees apart relative to the cirference of the tube.

With this coil and magnet configuration, the same concepts as described above can be used to reverse current direction in coils 192a and 192b for generation and detection of either torsional or flexural guided waves. A control unit 205, like that of FIG. 1B, is used to operate the MsT and to selectively reverse currents in at least one of the coils 192a and 192b.

What is claimed is:

1. A magnetosrictive transducer for testing a tubular structure when placed in a probe that moves along the length of the tubular structure, comprising:
a pair of electrically conductive coils wrapped around a shielding material;
wherein the coils are positioned 180 degrees apart relative to the inner circumference of the tubular structure, and each has a width corresponding to 30 degrees or less of the inner circumference of the tubular structure;
wherein each coil is wound in a direction parallel to the direction of motion of the probe;
a permanent magnet positioned between the coils, the permanent magnet being polarized in the direction of motion of the probe; and
a pulse generator electrically connected to each coil, operable to selectively activate the coils such that alternating current in the coils flows in the same direction or in opposite directions, thereby making the magnetostrictive transducer selectively operable to produce either flexural or torsional guided waves.

2. The magnetosrictive transducer of claim 1, wherein the shielding material is a ferromagnetic material.

3. A method of using magnetosrictive transducer for testing a tubular structure, comprising:
placing the magnetostrictive transducer in a probe, the probe operable to move along the length of the tubular structure;
wherein the magnetostrictive transducer comprises: a pair of electrically conductive coils wrapped around a shielding material; wherein the coils are positioned 180 degrees apart relative to the inner circumference of the tubular structure, and each has a width corresponding to 30 degrees or less of the inner circumference of the tubular structure; wherein each coil is wound in a direction parallel to the direction of motion of the probe; a permanent magnet positioned between the coils, the permanent magnet being polarized in the direction of motion of the probe;
selectively activating the coils such that alternating current in the coils flows in the same direction or in opposite directions at the same time, thereby making the magnetostrictive transducer selectively operable to produce either flexural or torsional guided waves; and
receiving the reflected flexural or torsional guided waves to determine the presence of a defect in the tubular structure.

4. The method of claim 3, further comprising the step of rotating the probe radially within the tube, and repeating the selectively activating and receiving steps.

5. A magnetosrictive transducer for testing a tubular structure when placed in a probe that moves along the length of the structure, comprising:
a pair of electrically conductive coils wrapped around a shielding material;
wherein the coils are positioned 180 degrees apart relative to the inner circumference of the tubular structure, and each has a width corresponding to 30 degrees or less of the inner circumference of the tubular structure;
wherein each coil is wound in a direction parallel to the direction of motion of the probe;
a pair of permanent magnets, with one of the pair of permanent magnets being positioned on one side of the coils and the other of the pair of permanent magnets being positioned on the other side of the coils, the permanent magnets being polarized in the opposite directions; and
a pulse generator electrically connected to each coil, operable to selectively activate the coils such that alternating current in the coils flows in the same direction or in opposite directions, thereby making the magnetostrictive transducer selectively operable to produce either flexural or torsional guided waves.

6. The magnetosrictive transducer of claim 5, wherein the shielding material is a ferromagnetic material.

7. A magnetosrictive transducer for testing a tubular structure, when placed in a probe that moves along the length of the structure, comprising:
an electrically conductive coil;
wherein the coil has windings positioned 180 degrees apart relative to the inner diameter of the tubular structure, and has a width corresponding to 30 degrees or less of the inner circumference of the tubular structure;
wherein the coil is wound in a direction parallel to the direction of motion of the probe;
a pair of permanent magnets, with one of the pair of permanent magnets being positioned on one side of the coil and the other of the pair of permanent magnets being positioned on the other side of the coil, the permanent magnets being polarized in opposite directions; and
wherein one of the pair of magnets is repositionable to change its polarization to either match that of the other of the pair of magnets or to be oppositely polarized, thereby making the magnetostrictive transducer selectively operable to produce either flexural or torsional guided waves.

8. A magnetosrictive transducer for testing a tubular structure, when placed in a probe that moves along the length of the structure, comprising:
an electrically conductive coil;
wherein the coil has windings positioned 180 degrees apart relative to the inner diameter of the tubular structure, and has a width corresponding to 30 degrees or less of the inner circumference of the tubular structure;
wherein the coil is wound in a direction parallel to the direction of motion of the probe;
a pair of permanent magnets, with one of the pair of permanent magnets being positioned within the coil and near one side of the coil and the other of the pair of permanent magnets being positioned within the coil and near the other side of the coil; and
wherein one magnet of the pair of magnets is repositionable to change its polarization to either match that of the other magnet of the pair of magnets or to be oppositely polarized, thereby making the magnetostrictive transducer selectively operable to produce either flexural or torsional guided waves.

9. A magnetosrictive transducer for testing a tubular structure, when placed on the outer surface of the tubular structure, comprising:
a pair of electrically conductive coils;
wherein each coil is wound in a direction parallel to the length of the tubular structure;
a pair of permanent magnets, with each magnet of the pair of permanent magnets being positioned such that one coil is between that magnet and the outer surface of the tubular structure;
wherein the coils are positioned 180 degrees apart relative to the outer circumference of the tubular structure, and each has a width corresponding to 30 degrees or less of the outer circumference of the tubular structure; and
wherein one magnet of the pair of magnets is repositionable to change its polarization to either match that of the other magnet of the pair of magnets or to be oppositely polarized, thereby making the magnetostrictive transducer selectively operable to produce either flexural or torsional guided waves.

* * * * *